（12）United States Patent
Chen et al.

(10) Patent No.: US 7,163,789 B2
(45) Date of Patent: Jan. 16, 2007

(54) CANCER DIAGNOSIS METHOD

(76) Inventors: Xu Qi Chen, University of Texas, MD Anderson Cancer Center, Leukemia Department, 1515 Holcombe Blvd., Houston, TX (US) 77030; Maurice Stroun, 6, rue Pedro-Meylan, CH-1208 Geneva (CH); Philippe Anker, Avenue Ernest-Pictet 15, CH-1203 Geneva (CH)

( * ) Notice: Subject to any disclaimer, the term of this patent is extended or adjusted under 35 U.S.C. 154(b) by 347 days.

(21) Appl. No.: 10/296,739

(22) PCT Filed: May 16, 2001

(86) PCT No.: PCT/IB01/00852

§ 371 (c)(1),
(2), (4) Date: May 13, 2003

(87) PCT Pub. No.: WO01/90409

PCT Pub. Date: Nov. 29, 2001

(65) Prior Publication Data

US 2004/0132019 A1    Jul. 8, 2004

(30) Foreign Application Priority Data

May 26, 2000    (EP) .................................. 00111370

(51) Int. Cl.
*C12Q 1/68*    (2006.01)
*C12P 19/34*    (2006.01)
(52) U.S. Cl. .................. 435/6; 435/91.1; 435/91.2; 435/91.21; 435/91.5; 435/91.51
(58) Field of Classification Search .................... None
See application file for complete search history.

(56) References Cited

U.S. PATENT DOCUMENTS

| | | | |
|---|---|---|---|
| 4,683,195 A | 7/1987 | Mullis et al. | |
| 4,699,877 A | 10/1987 | Cline et al. | |
| 4,874,858 A | 10/1989 | Magistro | |
| 4,999,290 A | 3/1991 | Lee | |
| 5,087,617 A | 2/1992 | Smith | |
| 5,098,890 A | 3/1992 | Gewirtz et al. | |
| 5,124,246 A | 6/1992 | Urdea et al. | |
| 5,155,018 A | 10/1992 | Gillespie et al. | |
| 5,217,889 A | 6/1993 | Roninson et al. | |
| 5,274,087 A | 12/1993 | Barnett et al. | |
| 5,300,635 A | 4/1994 | Macfarlane | |
| 5,409,818 A | 4/1995 | Davey et al. | |
| 5,470,724 A | 11/1995 | Ahern | |
| 6,132,965 A * | 10/2000 | Austin et al. ................... | 435/6 |
| 6,166,178 A * | 12/2000 | Cech et al. ................. | 530/324 |
| 6,329,179 B1 * | 12/2001 | Kopreski ................... | 435/91.2 |
| 6,607,898 B1 * | 8/2003 | Kopreski et al. .......... | 435/91.2 |
| 6,610,839 B1 * | 8/2003 | Morin et al. ............... | 536/24.1 |
| 6,821,726 B1 | 11/2004 | Dahm et al. | |

FOREIGN PATENT DOCUMENTS

| | | |
|---|---|---|
| DE | 3717212 A1 | 12/1988 |
| EP | 0 841 396 | 5/1998 |
| EP | 0 926 245 | 6/1999 |
| EP | 0 990 701 | 4/2000 |
| WO | WO 90/09456 A1 | 8/1990 |
| WO | WO 97/18322 | 5/1997 |
| WO | WO 97/35589 | 10/1997 |
| WO | WO 98/28442 | 7/1998 |
| WO | WO 99/40221 | 8/1999 |
| WO | WO 99/41406 | 8/1999 |

OTHER PUBLICATIONS

Kopreski et al. Clinical Cancer Research (1999) 5: 1961-1965.*
Gertler et al. Cancer. 2002. 95: 2103-2111, see p. 2104.*
Feng et al. Science. 1995. 269: 1236-1241.*
Kim et al. Science. 1994. 266: 2011-2015.*
Yajima et al., "Establishment of quantitative reverse transcription-polymerase chain reaction assays for human telomerase-associated genes", Clinica Chimica Acta, 290, 2000, pp. 117-127.
De Kok et al., "Real-Time Quantification of Human Telomerase Reverse Transcriptase mRNA in Tumors and Healthy Tissues", Clinical Chemistry, 46:3, 2000, pp. 313-318.
Shay, "Telomerase in Human Development and Cancer", Journal of Cellular Physiology, 173, 1997, pp. 266-270.
Kim et al., "Specific Association of Human Telomerase Activity with Immortal Cells and Cancer", Science, vol. 266, Dec. 23, 1994, pp. 2011-2015.
Novakovic et al., "Detection of telomerase RNA in the plasma of patients with breast cancer, malignant melanoma or thyroid cancer", Oncology Reports, vol. 11, 2004, pp. 245-252.
Miura et al., "Serum Human Telomerase Reverse Transcriptase Messenger RNA as a Novel Tumor Marker for Hepatocellular Carcinoma", Clinical Cancer Research, vol. 11, May 1, 2005, pp. 3205-3209.
Dragon et al., "In Vitro Assembly of Human H/ACA Small Nucleolar RNPs Reveals Unique Features of U17 and Telomerase RNAs", Molecular and Cellular Biology, vol. 20, No. 9, 2000, pp. 3037-3048.
Chen et al., "Telomerase RNA as a Detection Marker in the Serum of Breast Cancer Patients", Clinical Cancer Research, vol. 6, Oct. 2000, pp. 3823-3826.
Yi et al., "Both Transcriptional and Posttranscriptional Mechanisms Regulate Human Telomerase Template RNA Levels", Molecular and Cellular Biology, vol. 19, No. 6, Jun. 1999, pp. 3989-3997.
Kopreski et al., "Detection of Tumor Messenger RNA in the Serum of Patients with Malignant Melanoma", Clinical Cancer Research, vol. 5, Aug. 1999, pp. 1961-1965.
Bachand et al., "Expression of hTERT and hTR in *cis* reconstitutes an active human telomerase ribonucleoprotein", RNA, vol. 6, 2000, pp. 778-784.

(Continued)

*Primary Examiner*—Carla J. Myers
(74) *Attorney, Agent, or Firm*—Young & Thompson

(57) ABSTRACT

The invention concerns a method for the diagnosis and/or the follow up of the evolution of cancer comprising the analysis of the RNA components of the telomerase enzyme present in the plasma or serum of the blood.

20 Claims, No Drawings

OTHER PUBLICATIONS

Harrington et al., "A Mammalian Telomerase-Associated Protein", Science, vol. 275, Feb. 14, 1997, pp. 973-977.

Nugent et al., "The telomerase reverse transcriptase: components and regulation", Genes & Development, vol. 12, 1998, pp. 1073-1085.

Oulton et al., "Telomeres, telomerase, and cancer: life on the edge of genomic stability", Current Opinion in Oncology, vol. 12, 2000, pp. 74-79.

Anker, "Quantitative Aspects of Plasma/Serum DNA in Cancer Patients", Annals New York Academy of Sciences, pp. 5-7.

Joost, C.B.M. et al., Assembly of Transcriptionally Active RNA Polymerase I Initiation Factor SL1 from Recombinant Subunits, Science, vol. 266, Dec. 23, 1994.

Alkema et al., "Characterization and Chromosamal Localization of the Human Prata-Oncogene BMI-1," *Human Mol Genet* 2:1597-1603 (1993).

Aoki et al., "Liposome-mediated in viva gene transfer on antisense K-ras construct inhibits pancreatic tumor dissemination in the murine peritoneal cavity," *Cancer Research* 55:3810-3816 (1995).

Barz et al., "Characterization of Cellular and Extracellular Plasma Membrane Vesicles from a Non-metastasing Lymphoma (Eb) and Its Metastasing Variant (Esb)," *Biochin Biophys Acta* 814:77-84 (1985).

Bauer et al., "Identification of H-2Kb Binding and Immunogenic Peptides from Human Papillama Virus Tumour Antigens E6 and E7," *Scand J Immunol* 42:317-323 (1995).

Blackburn et al., "Electrochemiluminescence detection for development of immunoassays and DNA probe assays for clinical diagnostics," *Olin Chem* 37/9:1534-1539 (1991).

Bocchia et al., "Specific Binding of Leukemia Oncogene Fusion Peptides to HLA Class I Molecules," *Blood* 85:2680-2684 (1995).

Boom et al., "Rapid and Simple Method for Purification of Nucleic Acids," *J Clin Micro* 28:495-503 (1990).

Brossart et al., "Detection of residual tumor cells in patients with malignant melanoma responding to immunotherapy," *J Immunotherapy* 15:38-41 (1994).

Carr et al., "Circulating Membrane Vesicles in Leukemic Blood," *Cancer Research* 45:5944-5951 (1985).

Cheung et al., "Rapid and Sensitive Method for Detection of Hapatitis C Virus RNA by Using Silica Particles," *J Clin Micro* 32:2593-2597 (1994).

Chomczynski and Mackey, "Modification of the TRI reagent (TM) procedure for isolation of RNA from polysaccharide- and proteaglycan-rich sources," *Bio Techniques* 19:942-945 (1995).

Chomczynski and Mackey, "Substitution of chloroform by bromochloropropane in the single-step method of RNA isolation," *Analytical Biochemistry* 225:163-164 (1995).

Chomczynski et al., "Single-step method of RNA isolation by acid guanidinium thiocyanate-phenol-chloroform extraction," *Analytical Biochemistry* 162:156-159 (1987).

Chomczynski, "A reagent for the single-step simultaneous isolation of RNA, DNA and proteins from cell and tissue samples," *Biotech* 15:532-537 (1993).

Chu et al., "Thymidylate synthase binds to c-myc RNA in human colon cancer cells and in vitro," *Mol Cell Biol* 15:179-185 (1995).

Cohen, "Biochemical Therapy: Antisense Compounds," In: *Biologic Teraphy of Cancer* (DeVita, Hellman, Rosenberg, eds) J.B. Lippincott, Ca., Philadelphia (1991) pp. 763-775.

Colomer et al., "erB-2 antisense oligonucleotides inhibit the proliferation of breast carcinoma cells with erb-2 oncogene amplification," *Br J Cancer* 70:819-825 (1994).

Coutlee et al., "Immunodetection of DNA with biotinylated RNA probes: A study of reactivity of a monoclonal antibody to DNA-RNA hybrids," *Analytical Biochemistry* 181:96-105 (1989).

Datta et al., "Sensitive Detection of Occult Breast Cancer by the Reverse-transcriptase Polymerase Chain Reaction," *Journal of Clinical Oncology* 12:475-482 (1994).

Davidova and Shapot, "Liporibonucleoprotein Complex as an Integral Part of Animal Cell Plasma Membranes," *FEBS Lett* 6:349-351 (1970).

DiCesare et al., "A high-sensitivity electrochemiluminescense-based detection system for automated PCR product quantitation," *BioTechniques* 15:152-157 (1993).

Doi et al., "Detection of beta-human chorionic ganadotropin mRNA as a marker for cutaneoud malignant melanoma," *Int J Cancer* 65:454-45-. (1996).

Dosaka et al., "A complex pattern of translational initiation and phosphorylation in L-Myc Proteins," *Oncogene* 6:371-378 (1991).

Feng et al., "The RNA component of human telomerase," *Science* 269:1236-1241 (1995).

Fournie et al., "Recovery of nanogram quantities of DNA from plasma and quantitative measurement using labeling by nick translation," *Analytical Biochemistry* 158:250-256 (1986).

Gerhard et al., "Specific detection of carcinoembryonic antigen-expressing tumor cells in bone marrow aspirates by polymerase chain reaction," *J Clin Oncol* 12:725-729 (1994).

Ghossein et al., "Detection of Circulating Tumor Cells in Patients with Localized and Metastatic Prostatic Carcinoma: Clinical Implications," *Journal of Clinical Oncology* 13:1195-1200 (1995).

Hoon et al., "Detection of occult melanoma cells in blood with a multiple-marker polymerase chain reaction assay," *J Clin Oncol* 13:2109-2116 (1995).

Hoover et al., "Immunatherapy by Active Specific Immunization: Clinical Applications," In: *Biologic-Therapy of Cancer* (DeVita, Hellman, Rosenberg, eds) J.B. Lippincott, Co., Philadelphia (1991) pp. 670-682.

Imai et al., "Detection of HIV-1 RNA in Heparinized Plasma of HIV-1 Seropositive Individuals," *J Virol Methods* 36:181-184 (1992).

Jrdea et al., "Direct and quantitative detection of HIV-I RNA in human plasma with a branched DNA signal amplification assay," *AIDS* 7(suppl 2):S11-514 (1993).

Juckett and Rosenberg, "Actions of Cis-diamminedichloroplatinum on Cell Surface Nucleic Acids in Cancer Cells as Determined by Cell Electrophoresis Techniques," *Cancer Research* 42:3565-3573 (1982).

Kahn et al., "Rapid and sensitive nonradioactive detection of mutant K-ras genes via enriched PCR amplification," *Oncogene* 6:1079-1083 (1991).

Kamm and Smith, "Nucleic acid concentrations in normal human plasma," *Clinical Chemistry* 18:519-522 (1972).

Karet et al., "Quantification of mRNA in human tissue using fluorescent nested reverse-transcriptase polymerase chain reaction," *Analytical Biochemistry* 220:384-390 (1994).

Katz et al., "Enhanced Reverse Transcriptase-Polymerase Chain Reaction for Prostate Specific Antigen as a Indicator of True Pathologic Stage in Patients with Prostate Cancer," *Cancer* 75:1642-1648 (1995).

Kievits et al., "NASBA(TM) isothermal enzymatic in vitro nucleic acid amplification optimized for the diagnosis of HIV-1 infection," *J Virological Methods* 35:273-286 (1991).

Kim et al., "Specific association of human telomerase activity with immortal cells and cancer," *Science* 266:2011-2015 (1994).

Komeda et al., "Sensitive detection of circulating heptocellular carcinoma cells in peripheral venous load," *Cancer* 75:2214-2219 (1995).

Landgraf et al., "Quantitative analysis of polymerase chain reaction (PCR) products using primers labeled with biotin and a fluorescent dye," *Analytical Biochemistry* 193:231-235 (1991).

Larson et al., "Radioisotope Conjugates," In: *Biologic Therapy of Cancer* (DeVita, Hellman, Rosenberg, eds) J.B. Lippincott, Co., Philadelphia (1991) pp. 496-511.

Leon et al., "A Comparison of DNA and DNA-binding Protein Levels in Malignant Disease," *Europ J Cancer* 17:533-538 (1981).

Maruyama et al., "Detection of AMLi/ETO fusion transcript as a tool for diagnosing t(8;21) positive acute myelogenous leukemia," *Leukemia* 8:40-45 (1994).

Masella et al., "Characterization of Vesicles, Containing an Acylated Oligopeptide, Released by Human Colon Adenocarcinoma Cells," *FEBS Lett* 246:25-29 (1989).

McCabe et al., "Minimal Determinant Expressed by a Recombinant Viaccinia Virus Elicits Therapeutic Antitumor Cytolytic T Lumphocyte Responses," *Cancer Research* 55:1741-1747 (1995).

Miller et al., "Detection of minimal residual disease in acute promyelocytic leukemia by a reverse transcription polymerase chain reaction assay for the PML/RAR-alpha fusion mRNA," *Blood* 82:1689-1694 (1993).

Moore et al., "Design of PCR primers that detect only mRNA in the presence of DNA," *Nucleic Acids Research* 18:1921 (1991).

Mori, et al., "Detection of Cancer Micrometastases in Lymph Nodes by Reverse Transcriptase-Polymerase Chain Reaction," *Cancer Research* 55:3417-3420 (1995).

Mountford et al., "Proteolipid Identified by Magnetic Resonance Spectroscopy in Plasma of a Patient with Borderline Ovarian Tumor," *Lancet* i:829-834 (1987).

Nguyen, "Southern blot analysis of polymerase chain reaction products on acrylamide gels," *BioTechniques* 7:238-240 (1989).

Ozcelik et al., "Low Levels of Expression of an Inhibitor of Cyclin-dependent Kinases (CIP1/WAF1) in Primary Breast Carcinomas with p53 Mutations," *Clinical Cancer Research* 1:907-912 (1995).

Patard et al., "Expression of MAGE genes in transitional-cell carcinomas of the urinary bladder," *mt J Cancer* 64:60-64 (1995).

Penno et al., "Expression of CD44 in human lung tumors," *Cancer Research* 54:1381-1387 (1994).

Peoples et al., "Breast and Ovarian Cancer-Specific Cytotoxic T Lymphocytes Recognize the same HER-2/Neu Derived Peptide," *Proc Natl Acad Sci USA* 92:432-436 (1995).

Pfleiderer et al., "Detection of tumor cells in peripheral blood and bone marrow from ewing tumor patients by RT-PCR," *Int J Cancer (Pred. Oncol)* 64:135-139 (1995).

Polushin et al., "Antisense Pro-Drugs: 5'-ester oligodeoxynucleotides," *Nucleic Acids Research* 22:5492-5496 (1994).

Rashtchian, "Amplification of RNA," *PCR Methods Applic* 4:S83-S91 (1994).

Rieber and Bacalao, "An 'external' RNA removable from mammalian cells by mild proteolysis," *Proc Natl Acad Sci USA* 71:4960-4964 (1974).

Roggenbuck et al., "Human Papillomavirus Type 18 E6 and E6, and E7 Protein Synthesis in Cell Free Translation Systems and Comparison of E6 and E7 in Vitro Translation Products to Proteins Immunoprecipitated from Human Epthelial Cells," *J Viral* 65:5068-72 (1991).

Rosenberg-Nicolson et al., "Nucleoprotein Complexes Released from Lymphoma Nuclei that Contain the abl Oncogene and RNA and DNA Polymerase and RNA Primase Activities," *J Cell Biochem* 50:43-52 (1992).

Rosi et al., "RNA-Lipid Complexes Released from the Plasma Membrane of Human Colon Carcinoma Cells," *Cancer Lett* 39:153-160 (1988).

Saiki et al., "Genetic analysis of amplified DNA with immobilized sequence-specific oligonucleotide probes," *Science* 233:1076-1078 (1989).

Schlom, "Antibodies in cancer therapy: basic principles of monaclanal antibodies," In: *Biologic Therapy of Cancer*, (DeVita, Hellman, Hellman, Rosenberg, eds) J.B. Lippincott, Co., Philadelphia (1991) pp. 464-481.

Skorski et al., "Suppression of philadelphial leukemia cell growth in mice by BORABL antisense oligodeoxynucleotide," *Proc Natl Acad Sci USA* 91:4504-4508 (1994).

Sooknanan et al., "Detection and direct sequence identification of BCR-ABL mRNA in Ph+ chronic myeloid leukemia," *Experimental Hematology* 21:1718-1724 (1993).

Stock et al., "Value of molecular monitoring during the treatment of chronic myeloid leukemia: A cancer and leukemia group B study," *J Olin Oncology* 15:26-36 (1997).

Stroun et al., "Neoplastic characteristics of the DNA found in the plasma of cancer patients," *Oncology* 46:318-322 (1989).

Taylor and Blak, "Shedding of Plasma Membrane Fragments. Neoplastic and Developmental Importance," In: *The Cell Surface in Development and Cancer, Develop Biol* 3:33-57 Editor: M.S. Steinberg. Plenum Press, New York, London (1985).

Urdea et al., "Branched DNA amplification multimers for the sensitive, direct detection of human hepatitis viruses," *Nucleic Acids Research Symposium Series* 24:197-200 (1991).

Vandamme et al., "Detection of HIV-1 RNA in plasma and serum samples using the NASBA amplification system compared to RNA-PCR," *J Virological Methods* 52:121-132 (1995).

Vitetta et al., "Immunatoxins," In: *Biologic Therapy of Cancer* (DeVita, Hellman, Rosenberg, eds) J.B. Lippincott, Co., Philadelphia (1991) pp. 482-495.

Wang et al., "Quantitation of mRNA by the polymerase chain reaction," *Proc Natl Acad Sci USA* 86:9717-9721 (1989).

Wieczorek et al., "Diagnostic and Prognostic Value of RNA-Proteolipid in Sera of Patients with Malignant Disorders Following Therapy; First Clinical Evaluation of a Novel Tumor Marker," *Cancer Research* 47:6407-6412 (1987).

Wiedmann et al., "Ligase chain reaction (LCR)-overview and applications," *POR Methods Applic* 3:551-564 (1994).

Yanuck et al., "A Mutant P53 Tumor Suppressor Protein is a Target f or Peptide-Induced 0DB' Cytotoxic T-Cells," *Cancer Research* 52:3257-3261 (1993).

\* cited by examiner

SEQUENCE LISTING

```
<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaagggcgta ggcgccgtgc ttttgc                                          26

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtttgctcta gaatgaacgg tggaagg                                         27

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgacacctca cctcacccac                                                 20
```

```
<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cactgtcttc cgcaagttca c                                              21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cacctgcgac gatatttct                                                 19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgagggttgt acttagcca                                                 19

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggagtcaacg gatttggtcg tat                                            23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agccttctcc atggtggtga agac                                           24
```

CANCER DIAGNOSIS METHOD

This application is a national phase application of International Application No. PCT/IB01/00852, having an International Filing Date of May 16, 2001 which application claims priority under the terms of the Paris Convention and 35 U.S.C. §§ 120 and 361 to European Application No. EP 000111370.3, filed May 26, 2000, the disclosures thereof being explicitly incorporated by reference herein.

The present invention relates to a method of diagnosis and/or follow up of the evolution of several types of cancer, for instance after a chemotherapy or after an operation.

It is known that diagnosis and follow up of the evolution of cancers are carried out, besides direct observation of the tumors, by biopsy analysis or in the case of blood malignancies by analysis of the bone marrow, which implies either a surgical intervention, or an invasive test such as a biopsy or a bone marrow aspiration. Now, in addition to the disagreeable or even dangerous aspect of such methods, it has been observed that they could moreover not be very precise. In the case of breast cancer, great efforts have been made to develop a detection test by mammography. Although several studies indicate that mass mammography may be a useful strategy to reduce breast cancer mortality, this method involves a certain number of disadvantages. Amongst these, a high rate of false positives, frequent false negatives and enormous public health costs should be underlined. Thus, when the benefits are weighed against these advantages, it is not surprising that this form of screening has engendered contentious debates over the last twenty years.

The aim of this invention consists therefore in providing a method of diagnosis and/or follow up of the evolution of several types of cancers which would be, on one hand more precise and reliable and, on the other hand easier to perform without implying an invasive test for the patient.

The method of diagnosis and/or follow up of the evolution of cancer, object of the invention aiming to reach the above cited goal, includes the analysis of the RNA component and the mRNA coding for the proteins of the ribonucleoprotein telomerase in the blood plasma or serum.

Telomerase is a ribonucleoprotein enzyme that synthesizes repeated telomeric sequences at chromosomal ends. The telomeres protect the chromosomal ends and at each cell division these telomeres are shortened. Telomerase uses in order to synthesise these telomeres one or two segments of its RNA components as template.

The activity of this enzyme has become an accepted indicator for the diagnosis and the prognosis of most malignant tumors. The expression of human telomerase RNA (hTR) or of the reverse transcriptase enzyme of the RNA telomerase (hTERT) or/of the associated protein (TEP1) has been measured during the progression of several types of tumors. This has enabled the establishment of a correlation between this expression (the amount of RNA) and telomerase activity. Most cancers and immortalized cell lines have a high telomerase activity that reflects a mechanism that escapes normal aging regulations.

Now, although RNA components and mRNA coding for telomerase are cellular components, it was observed that, surprisingly, these components could be also found in an extracellular form in plasma or serum.

Indeed the present inventors have shown the presence of hTR, hTERT and TEP1 in the plasma or serum of persons suffering especially from breast, ovarian, stomach or colon cancers, while these products have been shown to be absent in the blood of healthy persons. Contrarily to several deoxyribonucleic acid (DNA) markers that has already been found in plasma or serum, such as Ras gene or P53 mutations or with the numerous the microsatellite sequences found in the literature, the telomerase RNAs seem to be able to be used for every kind of tumors. It appears to be a general plasmatic or serum cancer marker. Moreover for most cancers, the rate of sera bearing telomerase RNA is more important than the rate obtained with other nucleic acid markers used up to now.

More precisely, the method of diagnosis according to the invention consists in extracting the RNA from the plasma or the serum of the blood, purifying it and amplifying it in order to establish the presence and if necessary the quantity of the product made by the reverse polymerase chain reaction (RT-PCR) representing components hTR, hTERT or TEP1, this in a comparative manner between the plasma or serum of a person suspected of malignancy and the plasma or serum of a healthy person.

The PCR amplification products of the RNA components transcribed into DNA by the RT-PCR are detected and if necessary quantified using for instance gel coloration methods. This analysis can be performed also differently on other gels or without gel by a radioactive immunological technique (RIA), by ELISA (enzyme linked immunosorbant assay) or by a microchip test (gene array). A quantitative amplification on a Taq Man cycler (Perkin Elmer Biosystems) or a capillary Light Cycler (Hofmann La Roche) improves the precision of hTR. HTERT and TEP 1 detection.

Similarly, any technique of extraction of purification and of amplification of the RNA in the plasma or the serum may be used.

The present invention will now be illustrated in a non-limitative manner by the following Example related to breast cancer diagnosis. However, it must be stressed that the scope of the present invention is no way limited to the diagnosis of this type of cancer. Preliminary data have indeed also shown the presence of hTR, hTERT and TEP1 in the serum of patients suffering especially of ovarian or gastrointestinal cancers. On the basis of these results, it can be therefore concluded that hTR, hTERT and TEP1 in plasma or serum may constitute general markers for numerous types of cancers.

EXAMPLE

Diagnosis of breast cancer by the detection of hTR, hTERT or TEP1 in the plasma or serum of the blood.

Blood samples (2 to 3 ml) were collected prior to surgery on 18 patients bearing small malignant breast tumors (T1 or T2) still differentiated (G1 or G2) and without cancerous nodules nor metastases. After clotting, tubes were centrifuged at 900 g for 15 minutes at room temperature and serum collected. This was followed by a second 15 minutes centrifugation at 900 g to remove any cellular debris. Serum samples were stored at −70° C. until use.

RNA was extracted using a commercially available kit (SV Total RNA Isolation System, Promega, Madison, Wis.), according to manufacturer's instructions with a slight modification for serum or plasma samples: to each 100 µl serum or plasma were directly added 175 µl of SV RNA lysis buffer (only fresh or once frozen-thawed serum was used).

Detection of hTR, hTERT, TEP 1 and the rRNA (reference RNA) by the means of reverse transcriptase PCR (RT PCR):

The Qiagen One Step RT-PCR kit (Qiagen, Basel, Switzerland) was used to detect the presence and the quantity of hTR and GAPDH RNA in serum. 1 mg of tumor RNA was used in a 25 µl RT-PCR reaction mixture containing 400 µM of each dNTP, omniscript™ reverse transcriptase, sensiscript™ reverse transcriptase, hot-start Taq™ DNA polymerase and 0.15 µM primers i.e. for hTR(sense) GAAGGGCG-TAGGCGCCGTGCTTTTC (SEQ ID NO: 1) and(antisense) GTTTGCTCTAGAATGAACGGTG-GAAGG (SEQ ID NO: 2). The RT-PCT conditions of the mixture were an initial incubation at 50° C. for 30 min followed by a 95° C. incubation for 15 min to activate the HotstarTaq™ DNA Polymerase, then 50 cycles at 94° C. (30 sec), 65° C. (1 min), 72° C. (1 min) and a 10 minute final extension at 72° C.

RT-PCR conditions were identical for the detection of hTERT, except that 0.3 µM primer concentration was used, primers being (sense) TGACACCTCACCTCACCCAC (SEQ ID NO: 3) and (antisense) CACTGTCTTCCG-CAAGTTCAC (SEQ ID NO: 4).

The same conditions were used for the detection of TEP 1, primers being (sense) CACCTGCGACGATATTTCT (SEQ ID NO: 5) and (antisense) CGAGGGTTGTACT-TAGCCA (SEQ ID NO: 6) (primer concentration=0,3 µM).

In the case of control RNA, the same conditions were used for hTR were used with a primer concentration of 0,3 µM; the sequences of the GAPDH primers being(sense)GGAGT-CAACGGATTTGGTCGTAT (SEQ ID NO: 7) and (antisense) AGCCTTCTCCATGGTGGTGAAGAC (SEQ ID NO: 8).

All base sequences mentioned here above as primer examples are known and may as such be consulted on the web site of the Genome Database.

PCR amplification yielded products of 111 bp for hTR, 95 bp for hTERT, 150 bp for TEP1 and 306 bp for GAPDH RNA. Products were run at 55° C. on Elchrom Scientific S-50 gels (Elchrom Scientific, Cham, Switzerland), stained with SYBR-gold (Molecular Probes, Eugene, Oreg.-USA) for 45 min and destained twice in a darkroom for 30 min with deionized water at room temperature.

Results:

Using the technique described above, the result is that it is effectively possible to detect a PCR product of the reference RNA in all samples analysed. Quantitatively, all samples are similar whether they come from the serum of a healthy person or of a sick person.

In the case of the amplification product obtained with the specific amplimers for hTR, only the RNA of patients suffering of breast cancer was positive in 25% of the cases. The other RNA component of the enzyme hTERT was detected in 22% of the sera of patients. TEP 1 was detected in 20% of the cases. All together, the combination of the three markers has allowed th detection of breast cancer in 55% of the cases; this rate is clearly higher than the rate one may obtain with techniques known up to now that rarely exceed 30%. Moreover the RNA components of the telomerase are absent in the sera of the controls (healthy persons).

The invention claimed is:

1. A method of detecting human telomerase reverse transcriptase enzyme (hTERT) RNA extracted from plasma or serum from a human comprising:
   a) extracting a sample comprising extracellular RNA from plasma or serum of a human;
   b) amplifying said extracellular RNA for hTERT RNA to obtain an amplified product;
   c) detecting whether hTERT is present in the amplified product; and
   d) quantifying the amount of extracellular hTERT RNA in said sample, to thereby detect said hTERT RNA.

2. The method of claim 1, wherein said amplifying comprises reverse transcribing and amplifying the hTERT RNA in vivo.

3. The method of claim 2, wherein amplification is performed by polymerase chain reaction.

4. A method for detecting telomerase associated protein (TEP1) RNA in plasma or serum of a human comprising the steps of:

a) extracting a sample comprising extracellular RNA from plasma or serum of a human;
b) amplifying said extracellular RNA for TEP1 RNA;
c) detecting whether TEP1 is present in said sample; and
d) quantifying the amount of extracellular TEP1 RNA in said sample, to thereby detect said TEP1 RNA.

5. The method of claim 4, wherein said amplifying comprises reverse transcribing and amplifying the TEP1 RNA.

6. The method of claim 4, wherein amplification is performed by polymerase chain reaction.

7. A method for diagnosing or monitoring cancer in a patient, comprising:
extracting extracellular RNA from plasma or serum of the blood from said patient;
amplifying said extracellular RNA for an RNA component, wherein said RNA component is human telomerase reverse transcriptase enzyme (hTERT) RNA to detect whether said plasma or serum of the blood from said patient contains said RNA component;
quantifying the amount of said RNA component, if present, in said plasma or serum; and
comparing the amount of said RNA component in the plasma or serum of the blood from said patient to the amount of said RNA component in the plasma or serum of the blood a healthy person to diagnose or monitor cancer in said patient.

8. The method according to claim 7, further comprising detecting and quantifying the amount of GADPH RNA in the plasma or serum of the blood of the patient.

9. The method according to claim 7, further comprising detecting and quantifying the amount of human telomerase RNA (hTR) in the plasma or serum of the blood of the patient.

10. A method for diagnosing or monitoring cancer in a patient, comprising:
determining the level of extracellular human telomerase reverse transcriptase enzyme (hTERT) RNA in the plasma or serum of the blood of a patient having or suspected of having a malignancy, and comparing the level of said extracellular hTERT RNA in the plasma or serum of the blood of said patient to the level of extracellular hTERT RNA in the plasma or serum of the blood of a healthy person to thereby diagnose or monitor cancer in said patient.

11. The method according to claim 10, further comprising detecting and quantifying the amount of GADPH RNA in the plasma or serum of the blood of the patient.

12. The method according to claim 10, further comprising comparing the extracellular RNA levels of human telomerase RNA (hTR) from the plasma or serum of the blood of the patient having or suspected of having a malignancy to the extracellular RNA levels of hTR from the plasma or serum of the blood of a healthy person to diagnose or monitor cancer in said patient.

13. A method for diagnosing or monitoring cancer in a patient, comprising:
extracting extracellular RNA from plasma or serum of the blood from said patient;
amplifying said extracellular RNA for an RNA component, wherein said RNA component is telomerase associated protein (TEP1) RNA to detect whether said plasma or serum of the blood from said patient contains said RNA component;
quantifying the amount of said RNA component, if present, in said plasma or serum; and
comparing the amount of said RNA component in the plasma or serum of the blood from said patient to the amount of said RNA component in the plasma or serum of the blood a healthy person to diagnose or monitor cancer in said patient.

14. A method for diagnosing or monitoring cancer in a patient, comprising:
extracting extracellular RNA from plasma or serum of the blood from said patient;
amplifying said extracellular RNA for RNA components, wherein said RNA components are human telomerase reverse transcriptase enzyme (hTERT) RNA and telomerase associated protein (TEP1) RNA to detect whether said plasma or serum of the blood from said patient contains said RNA component;
quantifying the amount of said RNA components, if present, in said plasma or serum; and
comparing the amount of said RNA components in the plasma or serum of the blood from said patient to the amount of said RNA components in the plasma or serum of the blood a healthy person to diagnose or monitor cancer in said patient.

15. The method according to claim 13 or 14, further comprising detecting and quantifying the amount of GADPH RNA in the plasma or serum of the blood of the patient.

16. The method according to claim 13 or 14, further comprising detecting and quantifying the amount of human telomerase RNA (hTR) in the plasma or serum of the blood of the patient.

17. A method for diagnosing or monitoring cancer in a patient, comprising:
determining the level of extracellular telomerase associated protein (TEP1) RNA in the plasma or serum of the blood of a patient having or suspected of having a malignancy, and comparing the level of said extracellular TEP1 RNA in the plasma or serum of the blood of said patient to the level of extracellular TEP1 RNA in the plasma or serum of the blood of a healthy person to thereby diagnose or monitor cancer in said patient.

18. A method for diagnosing or monitoring cancer in a patient, comprising:
determining the level of extracellular RNAs in the plasma or serum of the blood of a patient having or suspected of having a malignancy, wherein said extracellular RNAs are human telomerase reverse transcriptase enzyme (hTERT) RNA and telomerase associated protein (TEP1) RNA, and comparing the level of said extracellular hTERT and TEP1 RNAs in the plasma or serum of the blood of said patient to the level of extracellular hTERT and TEP1 RNA in the plasma or serum of the blood of a healthy person to thereby diagnose or monitor cancer in said patient.

19. The method according to claim 17 or 18, further comprising detecting and quantifying the amount of GADPH RNA in the plasma or serum of the blood of the patient.

20. The method according to claim 17 or 18, further comprising comparing the extracellular RNA levels of human telomerase RNA (hTR) from the plasma or serum of the blood of the patient having or suspected of having a malignancy to the extracellular RNA levels of hTR from the plasma or serum of the blood of a healthy person to diagnose or monitor cancer in said patient.

* * * * *